US006602239B2

(12) United States Patent
Rönneklev

(10) Patent No.: US 6,602,239 B2
(45) Date of Patent: Aug. 5, 2003

(54) INFUSION BAG AND INFUSION SYSTEM

(75) Inventor: Pär Rönneklev, Hönö (SE)

(73) Assignee: Carmel Pharma AB, Gothenburg (SE)

( * ) Notice: Subject to any disclaimer, the term of this patent is extended or adjusted under 35 U.S.C. 154(b) by 0 days.

(21) Appl. No.: 09/844,217

(22) Filed: Apr. 27, 2001

(65) Prior Publication Data

US 2002/0099354 A1 Jul. 25, 2002

(30) Foreign Application Priority Data

Jan. 24, 2001 (SE) ............................................ 0100206

(51) Int. Cl.[7] ................................................ A61B 19/00

(52) U.S. Cl. ......................... 604/403; 604/408; 604/80; 604/89; 604/90

(58) Field of Search ......................... 604/80–83, 85–87, 604/88, 89–91, 93.01, 403–415; 222/500

(56) References Cited

U.S. PATENT DOCUMENTS 4,441,538 A * 4/1984 Larkin et al. ............... 604/415
4,460,365 A * 7/1984 Ganshirt et al. ............ 604/408
4,463,862 A * 8/1984 Hansen ........................ 215/50
4,479,989 A * 10/1984 Mahal ....................... 428/35.5
4,516,977 A * 5/1985 Herbert ...................... 604/415
5,971,181 A * 10/1999 Niedospial et al. ......... 215/247
6,179,821 B1 * 1/2001 Caspary et al. ............. 604/403
6,398,771 B1 * 6/2002 Gustafsson et al. ......... 383/209
2001/0012930 A1 * 8/2001 Ebner et al. ................ 604/250

* cited by examiner

*Primary Examiner*—Gregory L. Huson
*Assistant Examiner*—Amanda Flynn
(74) *Attorney, Agent, or Firm*—Norris McLaughlin & Marcus

(57) ABSTRACT

An infusion bag exhibiting an internal space which is surrounded by flexible walls, at least one outlet channel arranged through one of the walls for communication with the interior of the infusion bag, a communicating member integrated with the walls of the infusion bag which exhibits an opening accessible from the exterior of the infusion bag and an inlet channel which connects the opening with the interior of the infusion bag. An infusion system includes the infusion bag and a connecting member.

20 Claims, 3 Drawing Sheets

INFUSION BAG AND INFUSION SYSTEM

TECHNICAL FIELD

The present invention relates to an infusion bag in accordance with the preamble of claim 1, and an infusion system in accordance with the preamble of claim 10. Particularly, the invention relates to an infusion bag and an infusion system exhibiting a high degree of imperviousness against leakage when supplying medically effective substances to the infusion bag

BACKGROUND OF THE INVENTION

Infusion bags are utilized for intravenous delivery of fluids and medically effective substances to human beings or animals. For this reason, the infusion bag is provided with at least one outlet channel through which fluid can flow to a connecting device such as, for example, a cannula. When preparing the fluids which are to be administrated to the body from the infusion bag, it is common that medically effective substances are supplied to a pre-sealed infusion bag which is filled with a transport fluid, usually in the form of sodium chloride solution or a glucose solution. In certain cases, medically effective substances are harmful to other persons than the patient who has been prescribed predetermined doses as a result of an indication of a specific disease. This is particularly the case when long-term exposure is concerned, which can happen to medical staff when handling and preparing drugs for an extended period of time. For example, this is the case when preparing infusion bags containing cytotoxins, antibiotics and antiviral drugs. For this reason, there are special directions requiring preparation in safety cabinets and use of personal protective equipment, which implies that handling cannot take place without using these protective measures and devices. As a rule, the preparation is performed by means of injecting the medically effective substance through a membrane arranged in connection with an inlet channel arranged through the wall of the infusion bag. When performing this type of injection, leakage often occurs when the penetrating needle is withdrawn after having penetrated the membrane. Since the penetrating needle is often coarse, a major leakage may occur. A droplet of medically effective substance will be transported from the tip of the cannula 5 to the area surrounding the perforation in the membrane, at which leakage occurs.

SUMMARY OF THE INVENTION

Accordingly, it is an object of the present invention to reduce the risk of exposure to medically effective substances when preparing infusion bags. A second object is to provide infusion bags which enable the preparation to take place in any optional location without any leakage occurring, something which reduces staff resources needed for the preparation, reduces the preparation time; and also can provide treatment advantages and reduce the need of personal protective equipment and special peripheral equipment in the form of safety cabinets. The above-mentioned objects are achieved by means of an infusion bag according to the characterising portion of claim 1 and an infusion system according to the characterising portion of claim 8, by means of the infusion bag being provided with an inlet channel, arranged in connection with an integrated communicating member having an opening where a first flexible membrane is arranged in said opening to be accessible to a second flexible membrane arranged on a connecting member, and wherein said communicating member exhibits means for holding said second flexible membrane with a pressure against said first membrane, so that droplet formation on the surface of the first membrane is prevented, wherein occurrence of leakage after injection is prevented.

DESCRIPTION OF THE DRAWINGS

An embodiment of the invention will be described in greater detail with reference to the attached drawings, in which.

PREFERRED EMBODIMENT

Figure 1:
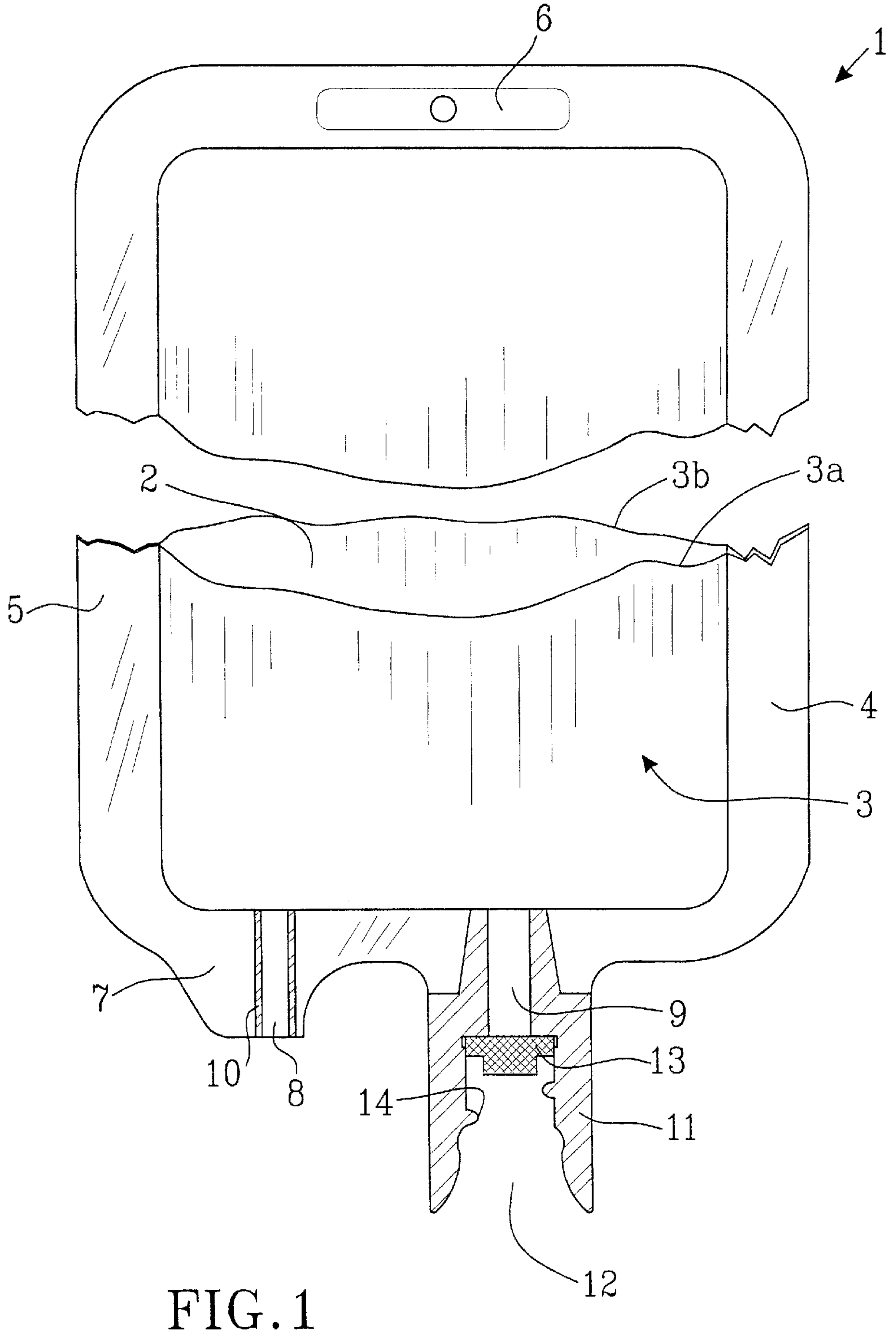
FIG. 1 shows a side view of an infusion bag.

FIG. 1 shows a side view of an infusion bag which is generally denoted with 1. The infusion bag 1 exhibits an internal space 2 which is surrounded by walls 3 of a preferably flexible material. According to one embodiment of the invention which is shown in FIG. 1, a front wall 3*a* is connected to a back wall 3*b* along two opposite side edges 4, 5, an upper edge 6 and a lower edge 7. The connection can be accomplished by means of welding or, alternatively, gluing. In this manner, the internal space 2 is formed between the joined edges 4–7. However, the invention is not limited to a special design of an infusion bag, but it can be manufactured in any way which is well-known to the skilled person. An outlet channel 8 and an inlet channel 9 are arranged through a wall of the bag 1. Preferably, said channels are arranged in connection with the lower edge 7 of the bag, which preferably is reinforced along the lower edge 7 in order to give stability to the outlet channel 8 and the inlet channel 9. In one embodiment of the invention, this has been achieved by means of a tube 10 which has been inserted and fixed between the front wall 3*a* and the back wall 3*b* to form an outlet channel 8. When mounted, the tube already can be provided with means for sealing the channel until use. These sealing means can be of any type well-known to the skilled person; alternatively the tube 10 can be sealed after having been mounted.

Figure 3A:
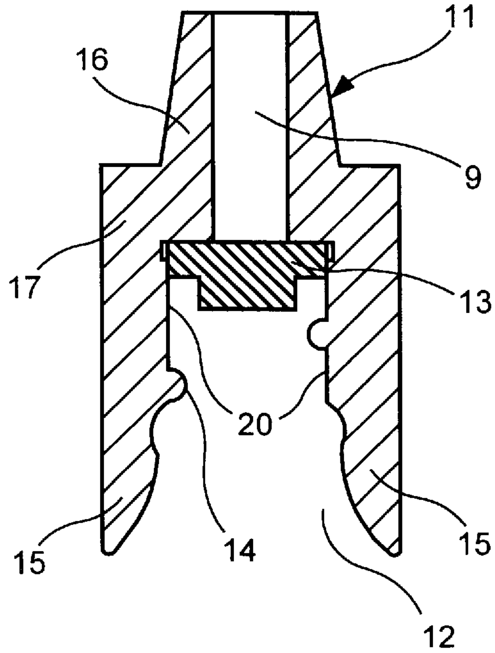
FIG. 3*a* shows a second embodiment of a communicating member.
Figure 3C:
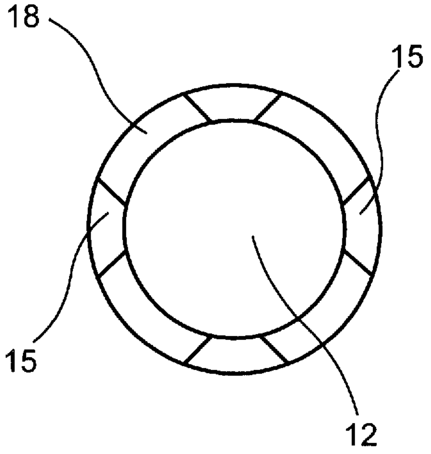
FIG. 3*c* shows a bottom view of the communicating member of FIG. 3*a*.
Figure 3B:
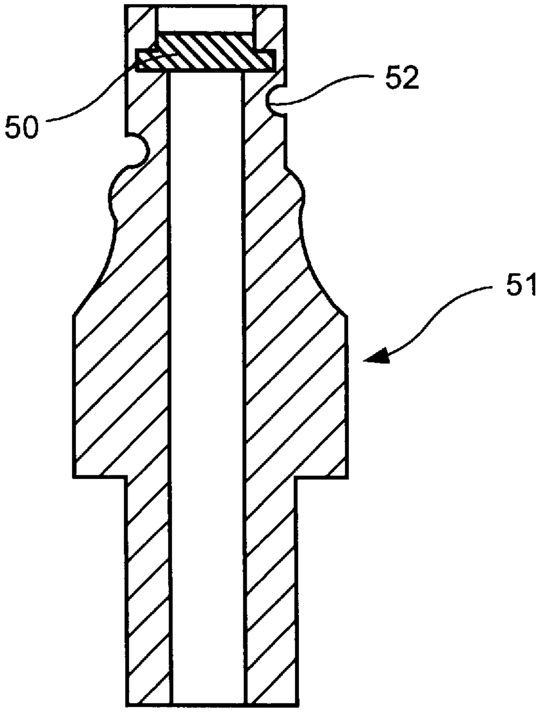
FIG. 3*b* shows a connecting member for use in combination with the communicating member of FIG. 3*a*.

Furthermore, the inlet channel 9 has been formed inside a communicating member 11. The communicating member is integrated with the walls of the infusion bag. This means that the communicating member is permanently fixed to the walls, either by means of the communicating member being integral with the walls, or the communicating member having been fixed by means of welding, gluing, or another permanent joint. The communicating member 11 exhibits an opening 12 through which a first flexible membrane 13 is arranged in an accessible way, wherein a second flexible membrane 50 arranged on a connecting member can be pressed against the first flexible membrane 13 forms a seal which prevents liquid from passing from the interior of the infusion bag to the environment. Furthermore, the communicating member 11 comprises means for holding said second flexible membrane 50 with a pressure against said first membrane 13. These means for holding can be constituted of, for example, a snap locking means having a resilient finger which engages a recess. The finger or the recess can be arranged on the communicating member, alternatively, the finger as well as the recess can be arranged on both the communicating member and the connecting member. In a preferred embodiment, which is shown in FIG. 3 (3*a,* 3*b*, 3*c*), these fingers surround said opening 12 and are aligned along the axis of symmetry of the opening. According to a preferred embodiment, said holding means comprise first guiding members 14 which are intended to interact with corresponding second guiding members 52 on said connecting member. Furthermore, said first guiding members exhibit a rest surface which forms an angle to a general plane of the axial extension of said opening, wherein said connecting member is intended to be transported along said axial extension in relation to the communicating member by means of rotation.

Figure 2A:
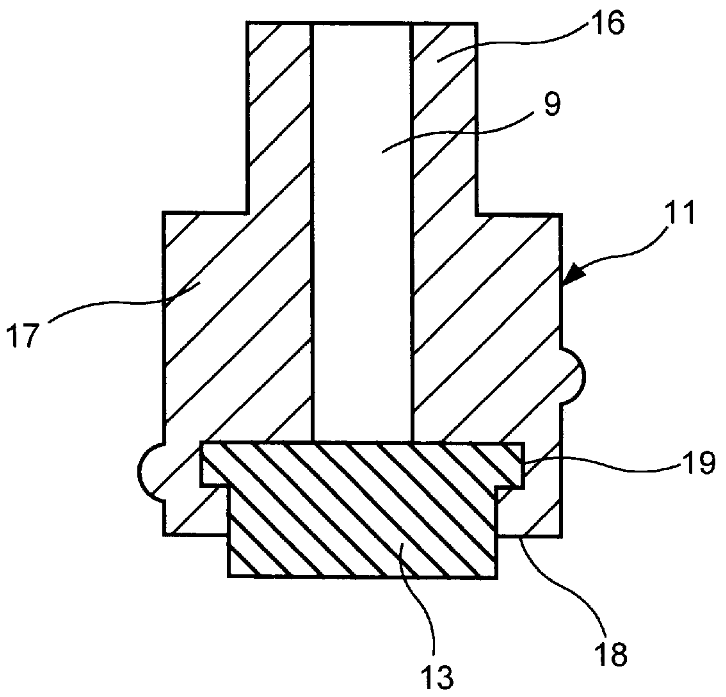
FIG. 2*a* shows a first embodiment of a communicating member.
Figure 2B:
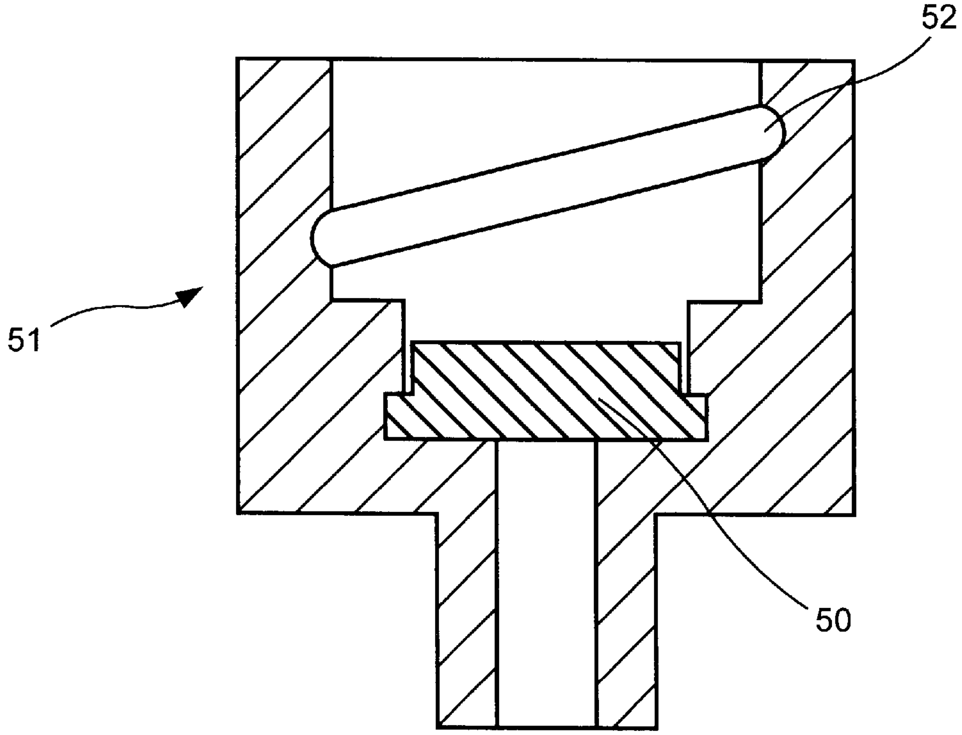
FIG. 2*b* shows a connecting member for use in combination with the communicating member of FIG. 2*a*.

FIGS. 2(2*a,* 2*b*) and 3 (3*a*, 3*b*, 3*c*) show alternative embodiments of the communicating member 11. In the embodiment shown in FIG. 2, the communicating member 11 is constituted by a substantially cylindrical body having an axial through-channel 9. The cylindrical body exhibits a first portion 16, which is intended to be permanently integrated with the walls of the infusion bag. Furthermore, the communicating member exhibits a second portion 17 which is intended to be connected to a connecting member 51. In a preferred embodiment, the diameter of the second portion 17 exceeds the diameter of the first portion, wherein a good sealing is achieved between walls and communicating member at the same time as the communicating member is easy to handle in relation to a connecting member. In the embodiment shown in FIG. 2, the first membrane is mounted superficially in connection with the first end surface 18 of the communicating member. The first membrane is fixed in the communicating member in a way well-known to the skilled person, for example by means of being fitted into a coaxially designed groove which is arranged in the channel 9. By means of this design, the communicating member is adapted to a connecting member 51 which is placed coaxially outside the communicating member.

In the embodiment shown in FIGS. 1 and 3, the first membrane 13 is placed in an opening 12. In this embodiment, the communicating member is adapted to a connecting member 51 which is placed coaxially against the inner walls 20 of the opening. For this reason, the opening 12 is designed as a cylindrical recess and exhibits said guiding members. The opening preferably exhibits a diameter which exceeds the diameter of the channel, preferably the diameter of the opening 12 is at least twice as large as the diameter of the channel 9. Furthermore, the embodiment according to FIG. 3 exhibits a number of fingers arranged on the first end surface 18 of the communicating member.

These fingers extend outwards from the surface in an axial direction. In a preferred embodiment of the invention, the fingers are bevelled in a direction away from this surface, wherein a conical guide for the connecting member, for centering this in relation to the communicating member, can be achieved.

In order to ensure that the locking of said first and second membranes takes place with a correct pressure between the two membranes 13, 50, said first guiding members exhibit an end stop which is intended to restrict the movement of said connecting member towards said membrane by means of a portion of the connecting member being pressed against said end stop.

In this context, "correct pressure" means that said locking means lock the connecting member against the communicating member when said first and second membranes have been pressed together up to a pressure exceeding the yield point of said membranes. This means that the membranes exhibit the same properties at the surfaces which have been pressed together as at another optional cross-section through the membranes, which implies that liquid cannot be pressed through the contact surfaces of the membranes. Such a property is obtained when said first and second membranes have been pressed together up to a pressure exceeding 150 kPa. According to a preferred embodiment, this yield point is reached by means of said locking means locking the connecting member against the communicating member when said connecting member has been pressed at least 1.4 mm in a direction towards said first membrane after reaching contact between said first membrane and said second member.

A series of tests have been performed on systems for leakage-proof transfer of fluids, comprising a connecting member and a communicating member exhibiting an inlet channel, a first flexible membrane separating said inlet channel from an opening of the communicating member, and means for holding a second membrane arranged on the connecting member with a pressure against said first membrane, by means of measuring the clamping force which has to be exceeded in order to press together the membranes until sufficient sealing is reached.

In these tests, a sufficient sealing has been reached with a compression within the interval 2.9–11.1 N, with a mean value of 7.6 N and a standard deviation of 1.7 N. This means that a preferred interval is between 5.9 and 9.3 N. The deformation length has been measured to be between 1.4 and 2.0 mm, preferably 1.7 mm. The membrane diameter is 5 mm and the membrane material is a type of elastomer. A more correct measure of when sufficient sealing will be obtained is the pressure with which the membranes contact each other. In a preferred embodiment, with the above-mentioned forces and membrane diameter, a sufficient sealing is obtained when the contact pressure exceeds 150 kPa. Since the device risks to be destroyed if it is subjected to exceedingly large contact forces, the contact pressure should be restricted as much as possible. In the same evaluation, it has been found that a sufficient sealing without any risk of failure is obtained with contact forces of up to 11.1 N, which corresponds to 565 kPa. Preferably, the contact pressure is within the interval 300–473 kPa.

What is claimed is:

1. An infusion bag having an internal space which is surrounded by flexible walls, at least one outlet channel arranged through one of said walls for communication with the interior of the infusion bag, and a communicating member integrated with the walls of the infusion bag, which communicating member exhibits an inlet channel connected with said internal space, wherein a first flexible membrane is arranged in connection with said inlet channel to be accessible to a second flexible membrane arranged on a connecting member, and that said communicating member exhibits means for holding said second flexible membrane with a pressure against said first membrane.

2. An infusion bag according to claim 1, wherein said first flexible membrane is mounted superficially.

3. An infusion bag according to claim 1, where the communicating member exhibits an opening accessible from the exterior of the infusion bag, and the inlet channel connects said opening with the interior of the infusion bag, wherein a first flexible membrane is mounted in said opening to be accessible to a second flexible membrane arranged on a connecting member, and that said communicating member exhibits means for holding said second flexible membrane with a pressure against said first flexible membrane.

4. An infusion bag according to claim 1, wherein said holding means comprise first guiding members which are intended to interact with corresponding second guiding members on said connecting member, and that said first guiding elements comprise a rest surface which forms an angle to a general plane of the axial extension of said opening, wherein said connecting member is intended to be transported along said axial extension in relation to the communicating member by means of rotation.

5. An infusion bag according to claim 4, wherein said guiding elements exhibit an end stop which is intended to restrict the movement of said connecting member towards said membrane by means of a portion of the connection member being pressed against said end stop.

6. An infusion bag according to claim 1, wherein said means for holding comprise a resilient locking member which locks the connecting member to the communicating member.

7. An infusion bag according to claim 1, wherein said means for holding are intended to lock the connecting member against the communicating member when said first and second membranes have been pressed together up to a pressure exceeding the yield point of said membranes.

8. An infusion bag according to claim 1, wherein said means for holding are intended to lock the connecting member against the communicating member when said first and second membranes have been pressed together up to a pressure exceeding 150 kPa.

9. An infusion bag according to claim 1, wherein said means for holding are intended to lock the connecting member against the communicating member when said connecting member has been pressed at least 0.2 mm in a direction towards said first membrane after reaching contact between said first membrane and second membrane.

10. An infusion system, comprising an infusion bag exhibiting an internal space which is surrounded by flexible walls, at least one outlet channel arranged through one of said walls for communication with the interior of the infusion bag, a communicating member integrated with the walls of the infusion bag which exhibits an inlet channel, and a connecting member which is connected to said communicating member, wherein a first flexible membrane is arranged in said opening, that said communicating member exhibits means for holding a second flexible membrane arranged on the connecting member with a pressure against said first membrane.

11. An infusion system according to claim 10, wherein said first flexible membrane is mounted superficially.

12. An infusion system according to claim 11, in which the communicating member exhibits an opening accessible from the exterior of the infusion bag, and the inlet channel connects said opening with the interior of the infusion bag, wherein a first flexible membrane is arranged in said opening to be accessible to a second flexible membrane arranged on a connecting member, and that said communicating member exhibits means for holding said second flexible membrane with a pressure against said first membrane.

13. An infusion system according to claim 10, wherein said holding means comprise first guiding members which are intended to interact with corresponding second guiding members on said connecting member, and that said first guiding elements comprise a rest surface which forms an angle to a general plane of the axial extension of said opening, wherein said connecting member is intended to be transported along said axial extension in relation to the communicating member by means of rotation.

14. An infusion system according to claim 13, wherein said guide members exhibit an end stop which is intended to restrict the movement of said connecting member towards said first flexible membrane by means of a portion of the connecting member being pressed against said end stop.

15. An infusion system according to claim 10, wherein said means for holding comprise a resilient locking member which locks the connecting member to the communicating member.

16. An infusion system according to claim 10, wherein said means for holding are intended to lock the connecting member against the communicating member when said first and second membranes have been pressed together up to a pressure exceeding the yield point of said membranes.

17. An infusion system according to claim 10, wherein said means for holding are intended to lock the connecting member against the communicating member when said first and second membranes have been pressed together up to a pressure exceeding 150 pKa.

18. An infusion system according to claim 10, wherein said means for holding are intended to lock the connecting member against the communicating member when said connecting member has been pressed at least 0.2 mm in a direction towards said first membrane after reaching contact between said first membrane and said second member.

19. A system for leakage-free transfer of fluid, said system comprising a connecting member and a communicating member which exhibits an inlet channel, a first flexible membrane which separates said inlet channel from an opening of the communicating member, and means for holding a second flexible membrane arranged on the connecting member with a pressure against said first membrane, wherein said locking means are intended to lock the connecting member against the communicating member when said first and second membranes have been pressed together up to a pressure exceeding 150 kPa.

20. A system according to claim 19, wherein said contact pressure is within the interval 150–565 kPa, preferably within the interval 300–473 kPa.

* * * * *